United States Patent
Harris et al.

(10) Patent No.: US 8,303,633 B2
(45) Date of Patent: Nov. 6, 2012

(54) DYNAMIC ANTERIOR VERTEBRAL PLATE

(75) Inventors: Peter M. Harris, Leesburg, VA (US);
Todd M. Wallenstein, Ashburn, VA (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 955 days.

(21) Appl. No.: 11/955,617

(22) Filed: Dec. 13, 2007

(65) Prior Publication Data
US 2009/0157121 A1    Jun. 18, 2009

(51) Int. Cl.
*A61B 17/80* (2006.01)
(52) U.S. Cl. .................................... 606/286; 606/289
(58) Field of Classification Search ............ 606/286, 606/289–290
See application file for complete search history.

(56) References Cited

U.S. PATENT DOCUMENTS

| | | | |
|---|---|---|---|
| 5,902,303 A * | 5/1999 | Eckhof et al. | 606/60 |
| 6,273,889 B1 * | 8/2001 | Richelsoph | 606/70 |
| 6,454,769 B2 * | 9/2002 | Wagner et al. | 606/279 |
| 6,679,883 B2 * | 1/2004 | Hawkes et al. | 606/279 |
| 6,695,846 B2 * | 2/2004 | Richelsoph et al. | 606/71 |
| 7,048,739 B2 * | 5/2006 | Konieczynski et al. | 606/288 |
| 7,524,325 B2 * | 4/2009 | Khalili | 606/290 |

* cited by examiner

*Primary Examiner* — Nicholas Woodall
(74) *Attorney, Agent, or Firm* — Carter, DeLuca, Farrell & Schmidt, LLP (57) ABSTRACT

Provided is a novel system that includes a low profile dynamic anterior vertebral body plate and bone screws for the fixation and stabilization of the cervical spine, the system having a locking element through which the bone screw passes, the locking element being capable of movement relative to the plate when the bone screws are fully inserted and in a locked position. Also provided is a method of stabilizing cervical vertebrae using the disclosed system.

18 Claims, 8 Drawing Sheets

FIG 1

FIG 2B
Detail A

FIG 6B
Detail B

FIG 8B
Detail C

DYNAMIC ANTERIOR VERTEBRAL PLATE

BACKGROUND OF THE INVENTION

1. Technical Field

The present invention relates to devices and methods for use in orthopedic spine surgery. In particular, the present invention relates to a system that provides a low profile dynamic anterior vertebral body plate for the secure fixation and stabilization of the cervical spine without the need for additional small locking parts while permitting limited motion of the anterior plate.

2. Background Art

Disease, the effects of aging, or physical trauma resulting in damage to the spine has been treated in many instances by fixation or stabilization of the effected vertebra. The use of plates and screws for fixation and stabilization of the cervical vertebra has been widely accepted as a reliable practice and has proven to be highly successful clinically.

The various plates, which are attached to the anterior vertebral bodies of the spinal column by bone screws have some common features such as relatively planar body profiles that define multiple holes or slots through which the screws fit and are threaded into the bone. A common result of the use of conventional anterior vertebral plates is a rigid fixation of the vertebrae. This rigid fixation is not always a preferred outcome, such as when some motion of the plate relative to the bone would be desirable in cases where the height of the intervertebral space changes or when compression of the space between the vertebral bodies is desired. Innovations over time have been primarily directed to improving the dependable security of the bone screw to the plate and as such have resulted in virtually complete rigidity of the screw, bone plate, bone connection. Various means have been used to prevent the screws from becoming loose or detached from their necessary secured or locked attachment to the vertebral plate. Among the differences between the conventionally used plates and screws is the manner in which the screws are locked into place in the hole or slot of the plate after the screws have been secured to the bone.

These conventional devices can be generally grouped into three basic categories with regard to how the screws are captured or secured in the plates.

Early plate designs were standard bone plates having holes through which screws were passed and screwed into the bone. These plates had no special provision for attaching the screws to the plate and as such were susceptible to having the screws back out of the plate over time. There have been clinically reported instances of screws backing out of these type plates with resulting surgical complications. Due to the potential and actual unreliable performance of such plates, the need for secure fixation of the screw to the plate as well as to the bone is now considered a basic requirement for vertebral plates. Due to the lack of predictable security of the screw to the plate, plates which do not secure the screw relative to the plate have fallen out of favor and virtually disappeared from use.

Various efforts have been made to secure the screws relative to the plates. In one design the screw head contains a threaded hole configured to receive a set screw. After the screw has been driven into bone and the head is seated in the plate hole, the set screw is inserted into the receiving hole of the screw head. The set screw is tapered to cause the screw head to expand and frictionally engage the wall of the plate hole, thereby resisting forces which tend to cause the screw to back out. While such mechanisms have worked to some degree, the addition of a small additional part, the set screw, at the time of surgery presents the potential hazard of dropping the set screw into the surgical field or otherwise misapplying the set screw to the screw head, for example, cross threading. Further, these types of plates have not allowed for any limited motion of the plate relative to the screw so as to allow for the dynamics of a change in height of the vertebrae or for compression of the vertebrae.

An alternative approach has been to provide features in the plate, which are specifically designed to hold the screw in position once the screw is inserted through the plate and screwed into the bone. One direction taken in this effort has been to design plates that incorporate or attach individual retaining rings or snap features associated with each plate hole configured to hold the inserted screw in place relative to the plate. These plates are very common and widely used; however, an inherent problem associated with such plates is the use of the additional very small retaining elements that can become disengaged from the plate and migrate into the surrounding soft tissues. Further, difficulty experienced in accessing and disengaging the small locking elements and removing the screws from this type of plate has caused some concern for the continued use of such plates. A similar approach involves individual cams associated with each plate hole, which when rotated apply friction pressure to the screw head in an attempt to resist back out.

Another approach is to add a cover to the plate after the screws have been placed. Such a design undesirably adds steps to the surgical procedure, thickness or height to the overall construct, and is susceptible to misapplication. Yet another direction taken in this effort to provide plates with locking elements is to provide dedicated overlying features, which are attached to the top side of the vertebral plate for the purpose of covering at least a portion of the screw head and thereby holding the screw in a seated and locked position. Generally these plates are designed to provide a variety of screw covering features that are pre-attached to the plate, and which can be selectively slid or rotated into position once it has been inserted. In some devices, such covering plates cover multiple screw heads. These plates typically require an increase in the overall composite thickness of the plate in order to accommodate the additional locking feature attached to the top side of the plate. This is a particularly unacceptable condition due to the use of such plates in an area of the spine where a thin, smooth surfaced profile for the plate assembly is preferred. Another major problem with such plates is that the overlying locking element cannot always be properly positioned over the screw head if the screw shaft was, due to anatomical necessity, positioned through the plate and into the bone at an angle such that the screw head does not fully seat in the plate recess provided on the top side of the plate. Further, when one of the overlying locking elements of such a plate loosens or becomes disengaged it is then tree to float away from the top side of the plate and migrate into the soft tissue adjacent to the top side of the vertebral plate.

Yet another approach is to provide machine threads in the plate hole with corresponding threads on the screw head. Thus the screw has a first, bone engaging thread on its shaft and a second machine thread on the screw head. As the thread shaft is screwed into bone the screw head approaches the plate hole and the machine thread engages the thread in the hole. This approach to securely locking the bone screw into the plate shares the common fault of the other approaches discussed above; after the screw is locked to the plate, there is no allowance for movement of the plate relative to the underlying bone. As indicated above, in some cases, limited movement is desired to accommodate for a change in height of the intervertebral space or when compression of the space between the vertebral bodies is desired.

Common to all of the conventional anterior vertebral bone plates is the goal to provide a rigid secure fixation of the plate to the anterior surface of the vertebrae. In that effort the principal focus of innovation has been to prevent the bone screw from backing out of its connection with the plate and thus permitting undesired and damaging movement of the plate relative to the vertebrae. In some cases, such as to allow for the dynamics of change in the height between vertebral bodies or when compression of the space between the vertebral bodies is desired, it is preferred to use a securely attached dynamic anterior vertebral plate that permits limited directional motion of the screws relative to the plate. None of the above described conventional efforts to provide a secure connection of the screw to the anterior plate have attempted to address the need in certain cases to provide a dynamic or semi-constrained anterior bone plate that is intended to permit limited movement of the screw and plate connection, while at the same time providing a secure connection of the screw to the plate.

There is therefore, an unfulfilled need for an anterior cervical plate system that can maintain a relatively low profile, as found in the non-locking plates while providing the security of a locking plate system. Further there is a need for a vertebral plate that does not have additional separate locking elements with the predictable problems of locking elements becoming disengaged from the plate and migrating away from the top side of the plate into the surrounding soft tissue. Finally, there is a need to provide a dynamic or semi-constrained anterior vertebral plate that when fixed to the vertebrae can permit limited motion of the plate relative to the screw so as to allow for a change in height of the intervertebral space when compression of the space between the vertebral bodies is desired.

SUMMARY OF THE DISCLOSURE

The present invention meets the above identified need by providing a low profile dynamic anterior vertebral body plate, which is secured to the underlying bone using a novel connection system.

Also provided is a low profile dynamic anterior vertebral body plate that is secured to the underlying bone using a novel bone screw and locking element connection system that permits limited motion of the screw relative to the plate.

Also provided is a low profile dynamic anterior vertebral body plate, the plate being secured to the underlying bone by bone screws, each of the screws having a locking feature that prevents the screw from backing out from the plate while permitting limited motion of the screw relative to the plate.

Also provided is a low profile dynamic anterior vertebral body plate having a slidably engaged locking element configured to receive and secure a bone screw, the locking element facilitating limited movement of the screw in relation to the plate.

Also provided is an alternative embodiment of the low profile dynamic anterior vertebral body plate having a pivotally engaged locking element configured to receive and secure a bone screw, the locking element facilitating limited movement of the screw in relation to the plate.

Also provided is a method of stabilizing spinal vertebrae while permitting limited motion of the plate connection to the bone screw, the method including providing a low profile dynamic anterior vertebral body plate, which is configured to be securely attached to the underlying bone of adjacent vertebrae using bone screws while being capable of limited motion in the bone screw plate connection.

Also provided is a kit, which includes at least one low profile dynamic anterior vertebral body plate and a corresponding set of bone screws.

BRIEF DESCRIPTION OF THE DRAWINGS

The foregoing and other features of the novel low profile dynamic anterior vertebral plate system will become apparent to one skilled in the art to which the disclosed system and devices relate upon consideration of the following description of exemplary embodiments with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figure 1:
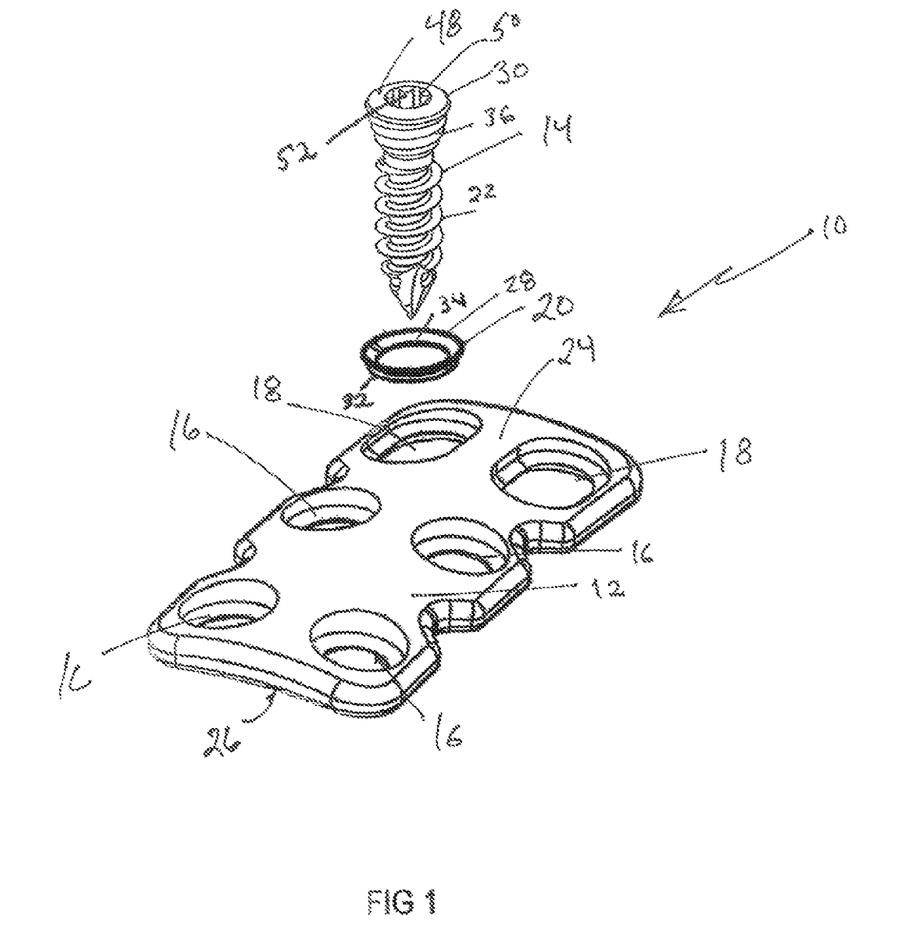
FIG. 1 shows an isometric view of the dynamic anterior plate system, the plate having six screw holes, two of which are elongated and four of which are circular. Also shown is a disassembled embodiment of the locking element configured to slide within the confines of one of the elongated screw holes. A bone screw is shown positioned over the locking element, the bone screw having bone engaging threads disposed distally along the screw shank for securing the plate to the underlying bone of the anterior surface of a vertebra and having plate locking threads disposed proximally on the screw shank and configured to interact with the inwardly projecting locking ridge of the locking element.
Figure 2A:
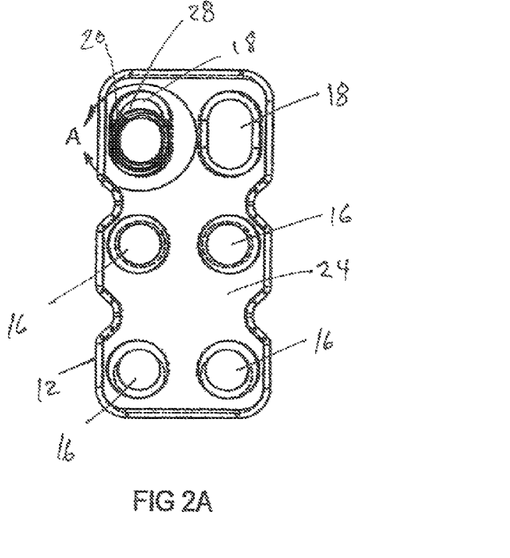
FIG. 2A shows a top view of the plate shown in FIG. 1 and illustrates the sliding engagement of the locking element within one of the elongated screw holes.
Figure 3A:
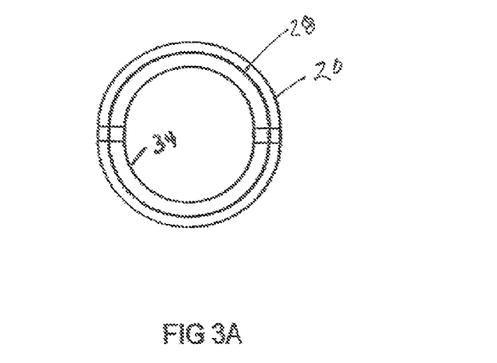
FIGS. 3A-B respectively show a top view and a side view of an elongated embodiment of the locking element shown in FIG. 2A-B.
Figure 3B:
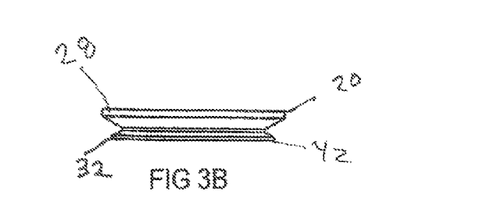
Figure 3C:
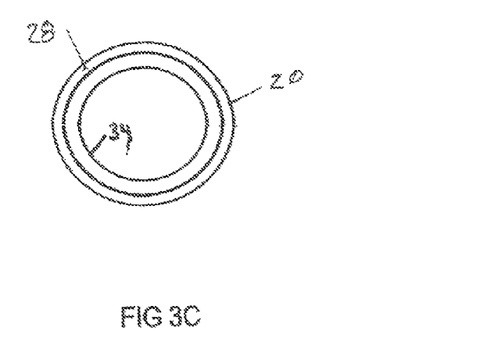
FIGS. 3C-D respectively show a top view and a side view of a circular embodiment of the locking element shown in FIG. 2A-B.
Figure 3D:
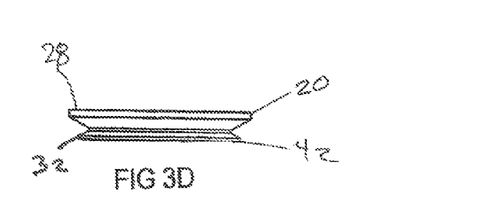
Figure 4A:
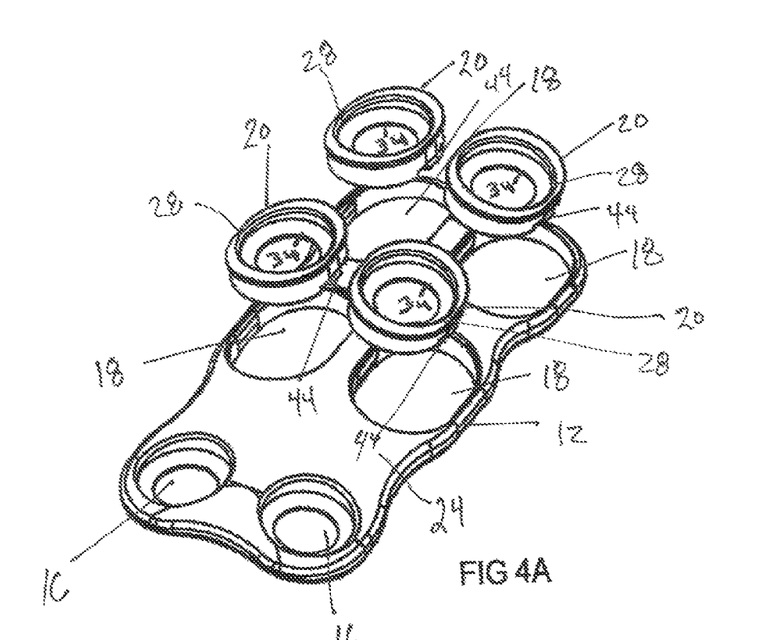
FIG. 4A shows an isometric view of the dynamic plate having six screw holes, two of which axe circular screw holes and four of which are elongated screw holes that are configured to receive a snap fit locking element illustrated disassembled and positioned over the four elongated screw holes.
Figure 10A:
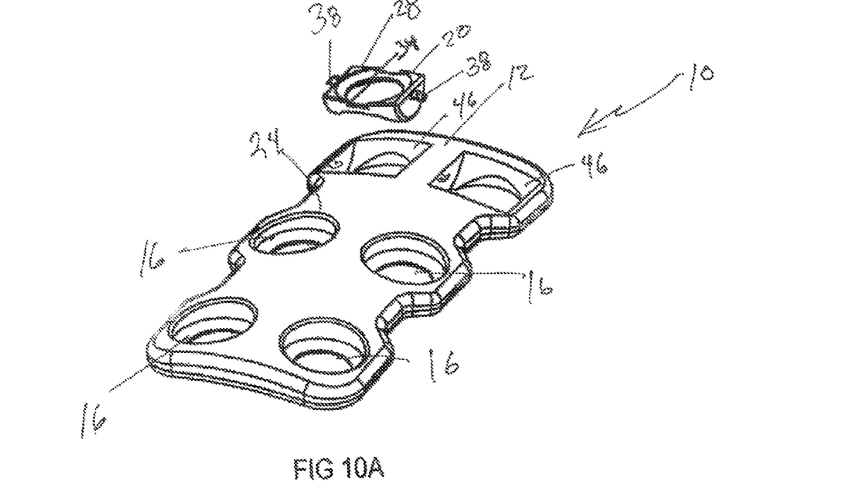
FIGS. 10A-C respectively show an alternative embodiment of the dynamic plate having two locking element articulation cradles having a generally arcuate shape and configured to pivotally engage a locking element having a complimentary shape and opposing pivot pins which engage the articulation cradles and facilitate rotational movement of the locking element therein.
Figure 10B:
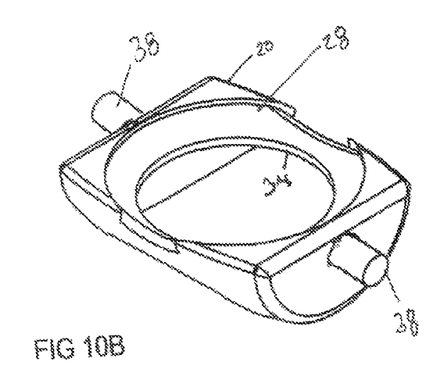
Figure 10C:
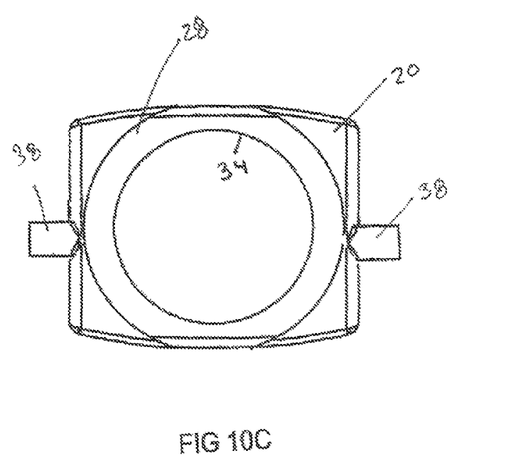

The dynamic anterior vertebral plate system, as generally shown at 10 in the accompanying figures, includes a low profile dynamic anterior vertebral body plate 12 that, when implanted in a patient, can be secured to the underlying bone using bone screws 14, such as those described in U.S. Pat. No. 6,322,562, the full disclosure of which is fully incorporated herein by reference. The vertebral body plate 12, as shown in FIGS. 1, 2A, 4A-B, 6A, 8A, and 10A can be provided as an elongated, low profile, plate structure that defines at least one and preferably multiple screw holes 16. The screw holes 16 can be configured to have a circular diameter or can be configured as elongated screw holes 18 as shown in FIGS. 1, 2A, and 4A. A locking element 20, which is sized and configured to permit through passage for the threaded portion 22 of the bone screw 14 from the plate upper surface 24 through the plate lower surface 26. The locking member 20 can be configured to have different shapes, such as for example, circular as shown in FIG. 3C, 4A-B, 5A-B, 6A, 7A, 8A-B, 9A-B, elongated, as shown in FIG. 3A, arcuate/cradle shaped as shown in FIG. 10A-C or of any shape that facilitates a secure connection to the bone screw 14 and a limited moveable engagement to the screw hole 16 or the elongated screw hole 18 of the plate 12.

As shown in FIGS. 1, 2A, 4A-B, 6A, 8A, and 10A the plate 12 can be configured to be generally planar; however, the plate can be formed to have arcuate upper and lower surfaces 24, 26, arcing along either or both the longitudinal axis and the transverse axis of the plate 12. Each of the elongated screw holes 18, as shown in FIGS. 2A-B and 4A-B, as defining through passages in the plate 12, are sized and configured to have a slidable engagement with a respective locking member 20. This sliding engagement permits limited sliding movement of the locking member 20 within the elongated screw hole 18. By this sliding engagement of the locking members 20 with the elongated holes 18, it is possible for the bone screws 14 to be fully inserted through the dynamic anterior plate and into the underlying bone material and still be capable of limited motion of the plate relative to the bone screws and the underlying vertebral bone tissue into which the screws 14 are firmly engaged. Thus, the dynamic anterior plate system is ideal for use in cases where limited motion is desirable, such as, for example, to accommodate a change in height of the intervertebral space or when compression of the space between the vertebral bodies is desired.

The locking member 20, at its upper portion 28 is configured to be generally circular and sized to circumferentially surround the screw head 30 when the screw 14 is fully seated in the locking member 20 and plate 12. The locking member 20, at its lower portion 32 is provided with an inwardly projecting screw engagement surface 34. This screw engagement surface 34 of the locking element 20 can be an inwardly projecting flange configured to lockably engage with a screw locking thread 36 located beneath the head of the screw 14 and above the threaded portion of the bone screw 14 that engages bone material when fully inserted through the plate 12. With reference to U.S. Pat. No. 6,322,562, which was above incorporated by reference, the locking element 20 engagement surface 34 can be configured to have a variety of shapes so long as the connection between the locking element 20 and the screw 14 is capable of providing a secure locking engagement.

As shown in FIGS. 6A-B, 7A-B, 8A-B, 9A-C and 10-A-C, the locking member 20 can alternatively be configured to articulate within the screw hole 16 with a rotating motion around the axis of a pivot pin 38 rather than with a sliding engagement in an elongated screw hole 18 as described above. Alternative embodiments, which provide for pivotal or rotational mechanisms instead of sliding mechanisms as shown in FIGS. 1, 2A-B and 4A-B to facilitate the limited movement of the plate 12 relative to the bone screw 14 are within the inventors' concept of providing limited motion through the limited motion of a locking element 20 with the plate 12.

As best shown in FIGS. 6A-B and 7A-B, the locking element 20 can be configured to define a pivot pin receiving groove 40, which is sized and configured to receive the complimentary pivot pin 38 extending inwardly from the interior wall of the screw hole 16. Reversal of these articulating elements, where as illustrated in FIGS. 8A-B, 9A-C and 10-B the locking element is provided with an outwardly projecting pivot pin 38 and the inward facing wall of the screw hole 16 defines a pivot pin receiving groove is within the inventor's concept.

Figure 2B:
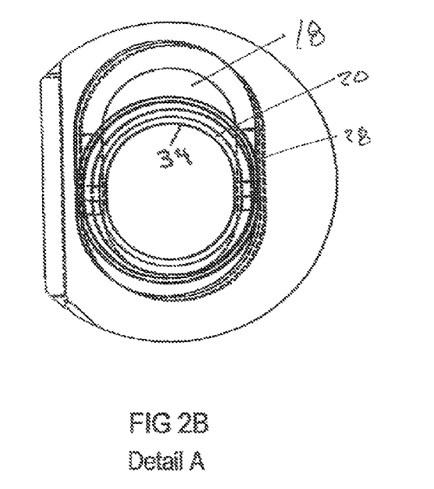
FIG. 2B shows an enlarged detail (A) of the dimensional relationship of the locking element to the elongated screw hole of FIG. 2A.
Figure 4B:
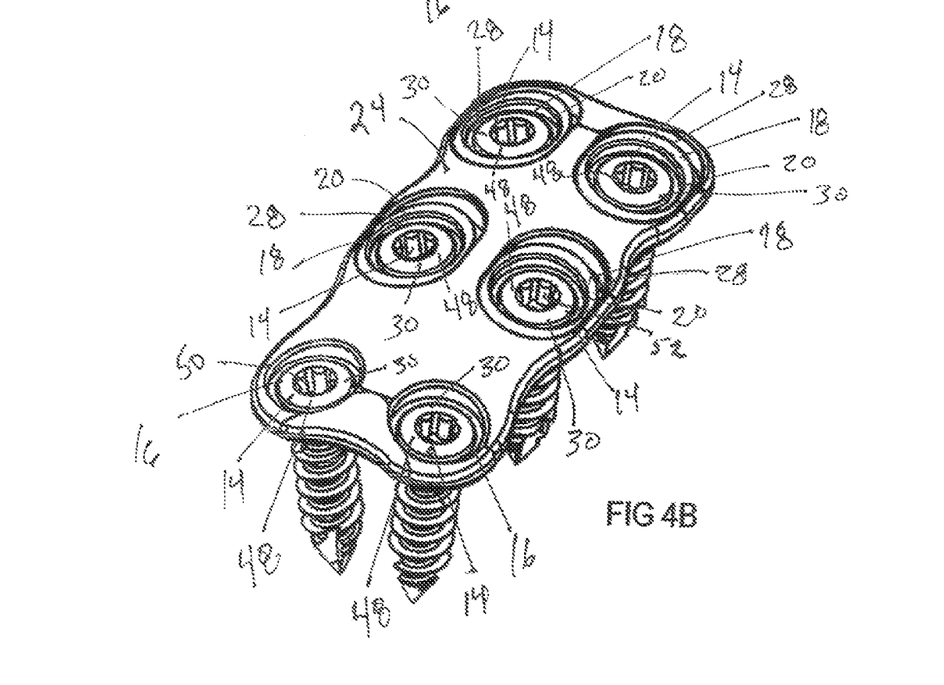
FIG. 4B shows an isometric view of the dynamic plate shown in FIG. 4A, the plate having six bone screws fully inserted into the plate.
Figure 5A:
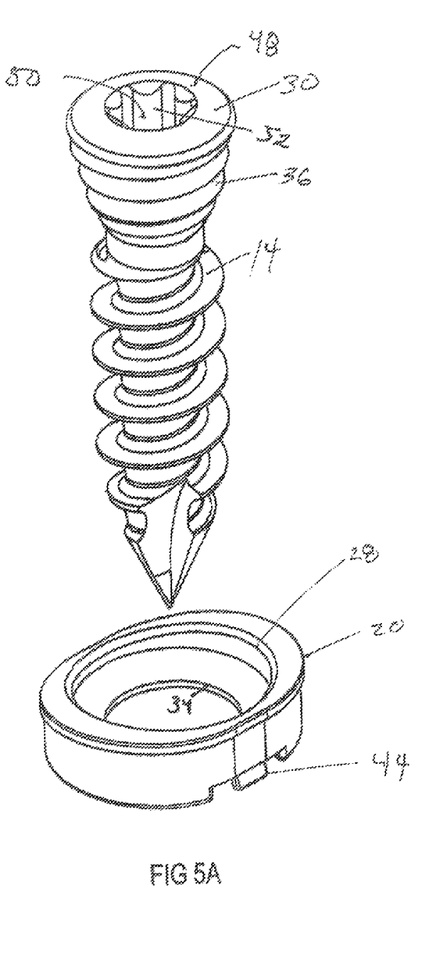
FIGS. 5A-B respectively show a bone screw positioned over the snap fit embodiment of the locking element shown in FIGS. 4A-B and the bone screw fully engaged in the locking element.
Figure 5B:
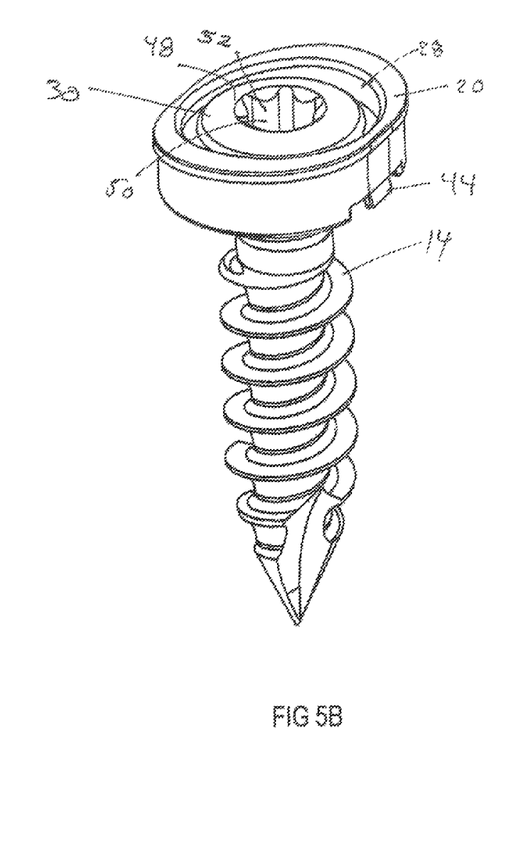
Figure 6A:
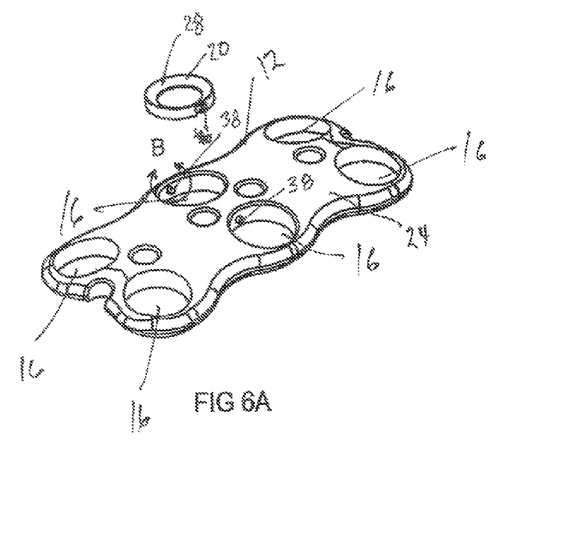
FIGS. 6A-B respectively show the dynamic plate with an alternative embodiment of the locking element connecting to the plate by a cam engagement with inwardly directed pins extending from the screw holes of the plate to facilitate pivotal movement of the locking element within the screw holes, a detail (B) of the pin being shown in FIG. 6B.
Figure 6B:
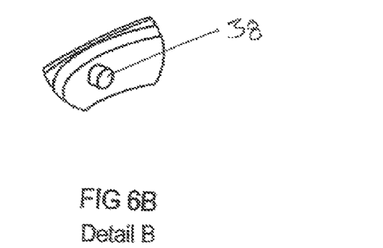
Figure 7A:
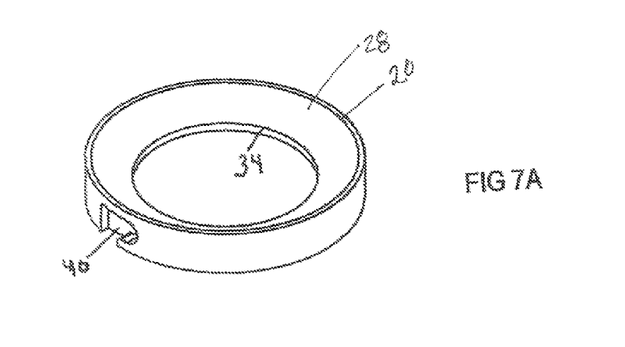
FIGS. 7A-B respectively show an isometric and a side view of the locking element illustrated in FIGS. 6A-B, the locking element illustrating the cam slot defined in the side wall of the locking element.
Figure 7B:
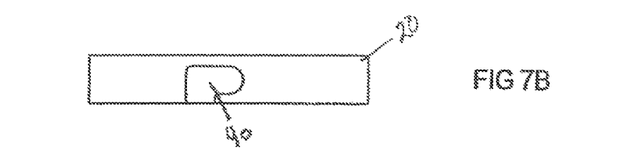
Figure 8A:
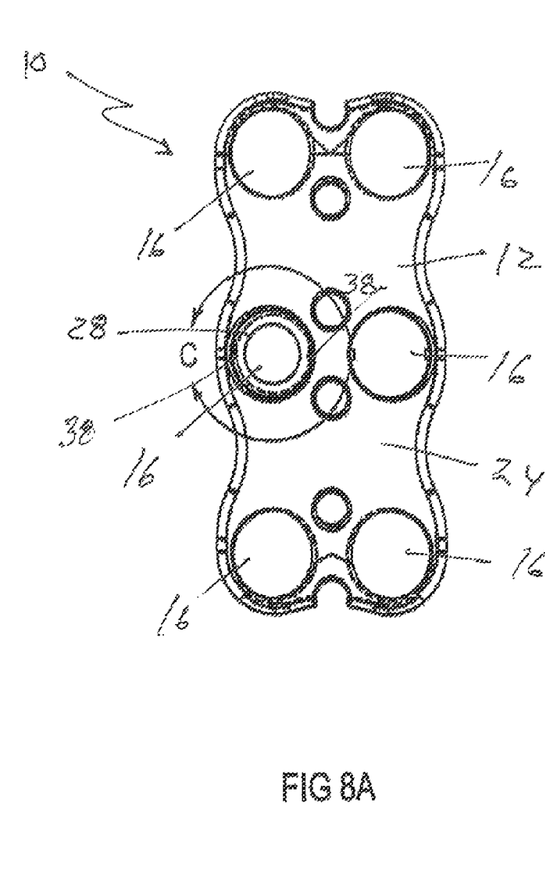
FIGS. 8A-B respectively show a top view of the dynamic plate having six circular screw holes and a detail (C) of a screw hole pivot pin engaging slot for receiving a locking element pivot pin.
Figure 8B:
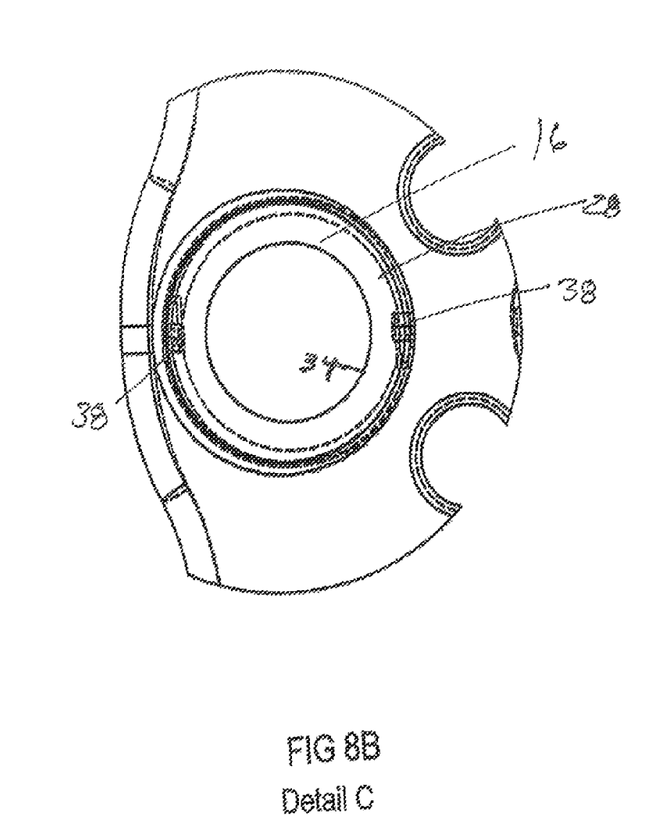
Figure 9A:
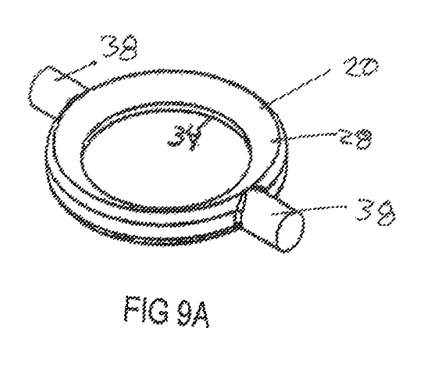
FIGS. 9A-C respectively show isometric, top, and side views of an alternative embodiment of a locking element having a pivot pin for engagement with a pivot pin engaging slot provided in the screw holes as illustrated in FIGS. 8A-B.
Figure 9B:
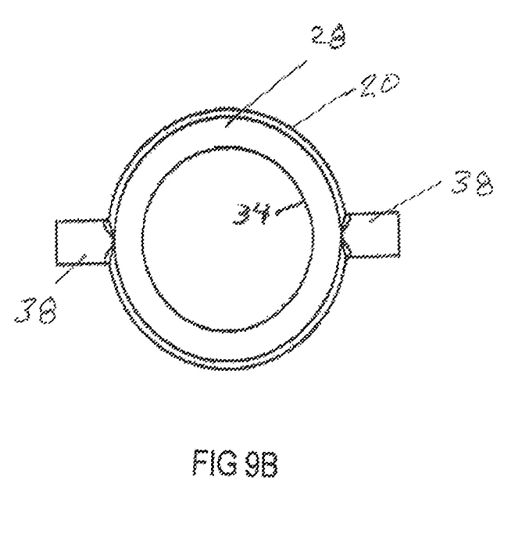
Figure 9C:
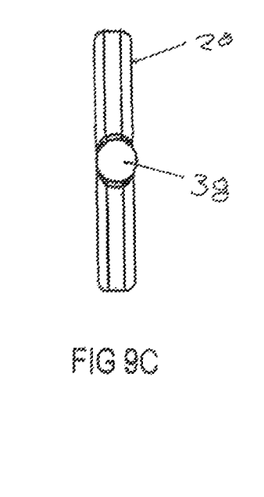

When assembling elements of the system 10, the locking element 20 can be cammed into the plate by insertion of the pivot pin 38 into the pivot pin receiving groove, which is best shown in FIGS. 7A-B. The locking element 20, when configured to have a sliding engagement with the plate 12, as shown in FIGS. 1, 2A-B and 4A-B be assembled with the plate 12 by any known assembly methods to include, for example, mechanical groove and flange as shown in FIGS. 1, 2A-B. The locking element, as shown in FIGS. 4A-B can be provided with a tab member 44, which can connect the locking member 20 to the elongated screw hole 28 by a snap fit mechanism. Another, non-limiting example of an alternative connection is shown in FIGS. 10A-C, where the plate 12 is shown with an arcuate or cradle shaped locking element articulation receptacle 46. In this alternative embodiment, the pivotally mounted locking element 20 is configured to have a complimentary cradle shape to facilitate rotational articulation with the plate 12. The above described alternative embodiments of articulating shapes and mechanisms are provided as non-limiting examples, which among others can be employed in the practice of the inventor's conception of a dynamic anterior vertebral plate.

Common to all embodiments of the inventors' dynamic anterior plate system 10 is the bone screw connection mechanism as defined in the incorporated U.S. Pat. No. 6,322,562 issued to Wolter. As described in the Wolter patent the locking connection of the screw to the plate is achieved by providing a threaded screw formed of a harder material than the plate or that portion of the plate, the deformable projection, which is to be deformed by the harder screw threads. By the incorporation of the concept of the Wolter patent disclosure into the present application, the locking element 20 or at least the screw engagement surface 34 of the locking element 20 can be formed of a softer material than that used to form the screw locking thread 36. While a preferred embodiment of the inventor's present concept of a dynamic anterior vertebral plate incorporates the technology of the fully incorporated Wolter patent, it is within the inventor's concept that alternative locking screws that would be capable of providing a locking interaction with the locking element 20 of the system 10 can be used.

As best shown in FIGS. 1, 4B and 5A-B, the upper surface 48 of the screw head 30 can define a tool receiving recess 50, which is sized and configured to operationally engage a tightening/loosening/removal tool as needed. Tool gripping elements 52 can be defined on the inner surface of the tool receiving recess 50, the gripping elements 52 being of a complementary shape to the tool being used. Any of a variety of known or novel shapes for gripping elements 52 can be used so long as they are complimentary to the shape of the tool employed. The inward or clockwise rotation of the tool can effectively drive the threaded portion 22 of the screw 14 into the bone.

This rotational movement of the tool and screw 14 can also serve to rotate the pin 38 into an operational connection within the receiving groove 40 for embodiments of the locking element 20 that are so equipped; a non-limiting example of which is shown in FIGS. 6A-B and 7A-B. Finally, when the screw 14 is fully seated in the locking element 20, the plate 10, and the underlying bone, the rotational movement of the screw 14 will have engaged the screw locking threads 36 with the locking member screw engagement surface 34.

The above described method of use of the system 10 can be employed as a method of stabilizing or fixing injured or diseased vertebrae and if necessary, multiple devices or a device, which is elongated beyond the examples depicted herein, can be employed as necessary.

While the device as described herein can be preferably used to attach to the anterior surface of cervical vertebrae and is configured to be capable of stabilizing cervical vertebrae, it is within the inventors' understanding that the plate can be configured and adapted to conform to any implantable surgical plate requirement to provide a low profile plate capable of securing and stabilizing any injured or diseased bone.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

It is also within the concept of the inventors to provide a kit, which includes at least one of the dynamic anterior vertebral plate and a complimentary number of bone screws. The kit can also include additional orthopedic devices and instruments; such as for example, instruments for tightening or loosening the bone screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A dynamic bone plate system, comprising:
a plate having an upper surface and a lower surface, said plate defining at least two bone screw holes, at least one unthreaded locking element configured to articulate with at least one of said at least two bone screw holes, at least two bone screws corresponding to said at least two bone screw holes, said bone screws being capable of securely connecting to said corresponding locking elements, wherein said locking elements include at least one tab member extending radially outward therefrom, the tab member configured to connect the locking elements to the corresponding one of the at least two bone screw holes such that the locking elements are capable of sliding movement relative to said plate when said screws are in a fully locked position,
wherein said bone screw has at least one locking thread disposed proximally of a threaded shaft of the bone screw for lockably engaging said unthreaded locking element,
wherein one of the bone screw holes is elongated and the tab of the locking element slidably engages an inner surface of the elongated bone screw hole such that when the bone screw is fully locked to the locking element, the plate is freely movable relative to the bone screw.

2. The bone plate system of claim 1, wherein said plate is an anterior vertebral body plate.

3. The bone plate system of claim 1, wherein said locking element defines a through passage sized and configured to allow passage of a portion of said bone screw, said portion being threads capable of engagement with bone material.

4. The bone plate system of claim 1, wherein said plate is configured to have an upper and lower curved surface, said curve being along the longitudinal axis of the plate.

5. The bone plate system of claim 4, wherein said curve is also along the transverse axis of the plate.

6. The bone plate system of claim 1, wherein said plate is configured to have an upper and lower curved surface, said curve being along the transverse axis of the plate.

7. The bone plate system of claim 1, wherein the tab of the locking element engages a substantially smooth surface of the elongated bone screw hole such that the locking element is freely movable in response to relative motion between the bone plate and the bone screw.

8. A method of stabilizing a vertebral body, the method comprising, providing bone plate system, comprising:
a plate having an upper surface and a lower surface, the plate defining at least two bone screw holes, at least one unthreaded locking element configured to articulate with at least one of the at least two bone screw holes, at least two bone screws corresponding to the at least two bone screw holes, the bone screws being capable of securely connecting to the corresponding locking elements, wherein the locking elements include at least one tab member extending radially outward, the tab member configured to connect the locking elements to the corresponding one of the at least two bone screw holes such that the locking elements are capable of bi-directional sliding movement relative to the plate when said screws are in a fully locked position, wherein said bone screw has at least one locking thread disposed proximally of a threaded shall of the bone screw for lockably engaging said unthreaded locking element;

surgically accessing an anterior surface of a vertebral body in need of stabilization; and positioning said bone plate and attaching same to said vertebral body.

9. A kit comprising:
a bone plate system, comprising:
a plate having an upper surface and a lower surface, the plate defining at least two bone screw holes, at least one unthreaded locking element configured to articulate with at least one of the at least two bone screw holes, at least two bone screws corresponding to the at least two bone screw holes, the bone screws being capable of securely connecting to the corresponding locking elements, wherein the locking elements include at least one tab member extending radially outward, the tab member configured to connect the locking elements to the corresponding one of the at least two bone screw holes such that the locking elements are capable of bi-directional sliding movement relative to the plate when said screws are in a fully locked position, wherein said bone screw has at least one locking thread disposed proximally of a threaded shaft of the bone screw for lockably engaging said unthreaded locking element; and
at least one other tool or instrument for use in orthopedic surgery.

10. A bone plate system, comprising:
a plate defining at least one bone screw hole;
at least one bone screw corresponding to the at least one bone screw hole, the at least one bone screw having a threaded head portion positioned proximal to a threaded shaft portion thereof; and
at least one locking element freely movable and slidably engageable with the at least one bone screw hole, the at least one locking element including an aperture having a threaded portion configured to releasably engage the threaded head portion of the at least one bone screw, the locking element including at least one tab member positioned distal to the threaded portion of the aperture and extending in a generally orthogonal direction relative to the axis of rotation needed to secure the at least one bone screw to the at least one locking element,
wherein said locking element is capable of bi-directional sliding movement relative to said plate when said bone screw is in a fully locked position,
wherein said bone screw has at least one locking thread disposed proximally of a threaded shaft of the bone screw for lockably engaging said locking element.

11. The bone plate system of claim 10, wherein the bone screw hole has a substantially smooth surface that interacts with the tab of the locking element such that the locking element is movable relative to the bone plate in response to relative motion between the bone plate and the bone screw.

12. A bone plate system comprising:
a plate defining at least one bone screw hole;
at least one bone screw corresponding to the at least one bone screw hole, the at least one bone screw having a threaded head portion positioned proximal to a threaded shaft portion thereof; and
at least one unthreaded locking element configured to engage the at least one bone screw hole, the at least one locking element including aperture having a lip to deformably engage the threaded head portion to lock the screw,
wherein said locking element is capable of sliding movement relative to said plate when said bone screw is in a fully locked position,
wherein said bone screw has at least one locking thread disposed proximally of a threaded shaft of the bone screw for lockably engaging said unthreaded locking element.

13. The plate of claim 12, wherein the locking element is made of a material that is less hard than the material of the screw.

14. The bone plate of claim 13, wherein the lip of the locking element extends inwardly.

15. The bone plate of claim 13, wherein the lip of the locking element is uninterrupted and engages the at least one locking thread of the bone screw.

16. A dynamic bone plate system, comprising:
a plate having an upper surface and a lower surface, said plate defining at least two bone screw holes, at least one unthreaded locking element configured to articulate with at least one of said at least two bone screw holes, at least two bone screws corresponding to said at least two bone screw holes, said bone screws being capable of securely connecting to said corresponding locking elements, wherein said locking elements include at least one tab member extending radially outward therefrom, the tab member configured to connect the locking elements to the corresponding one of the at least two bone screw holes such that the locking elements are capable of sliding movement relative to said plate when said screws are in a fully locked position, wherein said bone screw has at least one locking thread disposed proximally of a threaded shaft of the bone screw for lockably engaging said unthreaded locking element,
wherein the locking element includes a lip extending inwardly towards a passage extending through the locking element.

17. The bone plate system of claim 16, wherein the lip is continuous for engaging the locking thread of the bone screw.

18. The bone plate system of claim 17, wherein the locking element includes a first material and the locking thread of the bone screw includes a second material, the second material being harder than the first material.

* * * * *